(12) United States Patent
Peng (10) Patent No.: US 12,225,171 B2
(45) Date of Patent: Feb. 11, 2025

(54) F-MODE DISPLAY OF ULTRASOUND IMAGES FOR CHARACTERIZATION OF TISSUE STRUCTURES AND PROPERTIES

(71) Applicant: CLOUDSTREAM MEDICAL IMAGING, INC., Houston, TX (US)

(72) Inventor: Chengbin Peng, Houston, TX (US)

(73) Assignee: CLOUDSTREAM MEDICAL IMAGING, INC., Houston, TX (US)

( * ) Notice: Subject to any disclaimer, the term of this patent is extended or adjusted under 35 U.S.C. 154(b) by 96 days.

(21) Appl. No.: 17/963,262

(22) Filed: Oct. 11, 2022

(65) Prior Publication Data

US 2023/0117281 A1 Apr. 20, 2023

Related U.S. Application Data

(60) Provisional application No. 63/255,703, filed on Oct. 14, 2021.

(51) Int. Cl.
*H04N 1/60* (2006.01)

(52) U.S. Cl.
CPC ......... *H04N 1/6005* (2013.01); *H04N 1/6008* (2013.01)

(58) Field of Classification Search
CPC ...... H04N 1/6005; H04N 1/6008; H04N 1/60; A61B 8/06; A61B 8/461; A61B 8/488; A61B 8/5207; G06T 11/206
See application file for complete search history.

(56) References Cited

U.S. PATENT DOCUMENTS

| 2009/0016587 A1* | 1/2009 | Strobel | G06T 7/20 |
| | | | 382/130 |
| 2022/0249054 A1* | 8/2022 | Parker | A61B 8/085 |

FOREIGN PATENT DOCUMENTS

| AU | 2019100734 A4 * | 8/2019 | |
| WO | WO-9621215 A1 * | 7/1996 | ............... A61B 8/06 |

* cited by examiner

*Primary Examiner* — Jeffery A Brier
(74) *Attorney, Agent, or Firm* — SZDC Law PC (57) ABSTRACT

A method for generating F-mode display of an ultrasound image includes: collecting ultrasound image data that include a plurality of physical properties; mapping the physical properties to a plurality of color components of a color space; and combining the color components to generate an F-mode display of the ultrasound image. Each of the physical properties corresponds a corresponding color component.

9 Claims, 6 Drawing Sheets
(2 of 6 Drawing Sheet(s) Filed in Color)

F-MODE DISPLAY OF ULTRASOUND IMAGES FOR CHARACTERIZATION OF TISSUE STRUCTURES AND PROPERTIES

This application claims priority to U.S. Provisional Patent Application No. 63/255,703, filed on Oct. 14, 2021, which is incorporated by reference for all purposes as if fully set forth herein.

FIELD OF THE INVENTION

The present invention relates to a method for generating F-mode display of ultrasound images for characterization of tissue structures and properties.

BACKGROUND OF THE INVENTION

An ultrasound scanner produces pictures of the inside of human body using sound waves. It uses a small probe called a transducer and gel placed directly on the skin. High-frequency sound waves travel from the probe through the gel into the body. The probe collects the sounds that bounce back. Ultrasound signals contain information about mechanical and acoustic properties of tissues and organs through which the ultrasound waves propagate or from which ultrasound waves are reflected. Those sound waves are used to create an image. Ultrasound imaging is a noninvasive medical test that helps physicians diagnose and treat medical conditions [1,2].

The first generation of commercial ultrasound scanners in 1950s used A-mode display of ultrasound data. In 1970s the second generation of commercial ultrasound scanners used B-mode display of ultrasound images. Color Doppler scanners came into the market in 1980s which produced color images of blood flow on top of B-mode display. This is the third generation of commercial ultrasound scanners. In 1990s and early 2000s software based beamformers were developed to replace hardware-based beamforming [3]. At the same time elastography scanners came to the market which produced color images of tissue stiffness on top of B-mode display (also called E-mode). This is the fourth generation of commercial ultrasound scanners. Recently commercial ultrasound scanners of the fifth generation are released into the market in which data processing and beamforming are implemented on GPUs, yielding much improved ultrasound images in real time [4].

The widely used B-mode display could not tell, besides echo strength, other important properties that are needed to characterize health of tissues, such as, hardness of the tissues, mass density, sound speed, Poisson's ratio, mechanical moduli, water content, and acoustic attenuation coefficient. Attempts were made to measure physical tissue properties using ultrasound. Travel time tomography was used to invert for sound speed in tissues. It uses the travel time between a pair of transmitter and receiver [5, 6]. Reflection tomography was also used to estimate sound speed distribution in tissues [7]. Shear wave elastography was another example. It uses shear wave fronts excited by a moving focused ultrasound to measure shear wave speeds [8, 9]. Diffraction tomography was used for breast imaging. It uses diffracted waves to invert for compressional wave speed distribution in the breast tissues [10]. Full waveform inversion was also reported in literature where a super-computer was used to invert for compressional wave speed variations by exactly matching recorded waveforms with computer generated waveforms [11]. Recently real time inversion of sound speed and Poisson's ratio during beamforming was also disclosed [12].

These methods extend ultrasound use to detailed characterization of physical properties of tissues and organs. In such a way we can obtain not only a reflectivity image using an ultrasound scanner but also other useful physical properties such as Poisson's ratio and sound speed at every image point in real time. The present invention describes a novel method to co-render the reflectivity image and two property values together to aid in detailed characterization of tissues and organs inside human and animal bodies.

SUMMARY OF THE INVENTION

In one embodiment, the present application discloses a method for generating F-mode display of an ultrasound image. The method includes: collecting ultrasound image data that include a plurality of physical properties; mapping the physical properties to a plurality of color components of a color space; and combining the color components to generate an F-mode display of the ultrasound image. Each of the physical properties corresponds a corresponding color component.

In another embodiment, an increase of a value of the corresponding color component corresponds to an increase or decrease of a value of the each of the physical properties.

In another embodiment, the physical properties include three or more selected from the group consisting of acoustic reflectivity, acoustic attenuation coefficient, sound speed, Poisson's ratio, shear wave speed, porosity and fluid saturation, density, micro movement of tissue, gas bubble flow, and blood flow.

In another embodiment, the color space is a YCbCr color space or an RGB color space.

In another embodiment, three physical properties selected from the group consisting of acoustic reflectivity, acoustic attenuation coefficient, sound speed, and Poisson's ratio, shear wave speed, porosity and fluid saturation, density, micro movement of tissue, gas bubble flow, and blood flow are mapped to corresponding color components of the color space.

In another embodiment, the color space is the YCbCr color space, and the YCbCr color space includes an intensity component (Y), a red chrome component (Cr), and a blue chrome component (Cb).

In another embodiment, the color space is the RGB color space, and the RGB color space includes a red component (R), a green component (G), and a blue component (B).

In another embodiment, the three physical properties are the reflectivity, the sound speed, and the Poisson's ratio; and the reflectivity is mapped to the intensity component, the sound speed is mapped to the red chrome component, and the Poisson's ratio is mapped to the blue chrome component.

In another embodiment, the three physical properties are the reflectivity, the sound speed, and the Poisson's ratio; the reflectivity is mapped to the red component, the sound speed is mapped to the green component, and the Poisson's ratio is mapped to the blue component.

In another embodiment, the present invention discloses an ultrasound image processing apparatus that includes an image processor adapted to: collecting ultrasound image data that include a plurality of physical properties; mapping the physical properties to a plurality of color components of a color space; and combining the color components to generate an F-mode display of the ultrasound image. Each of the physical properties corresponds a corresponding color component.

It is to be understood that both the foregoing general description and the following detailed description are exemplary and explanatory and are intended to provide further explanation of the invention as claimed.

BRIEF DESCRIPTION OF THE DRAWINGS

The patent or application file contains at least one drawing executed in color. Copies of this patent or patent application publication with color drawings will be provided by the Office upon request and payment of the necessary fee.

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

The present invention proposes a novel method of co-rendering three physical properties in one color image for detailed characterization of tissues and organs. We call this rendition of ultrasound images an F-mode display. In one embodiment we co-render into one color image reflectivity values, Poisson's ratio values, and sound speed values. In another embodiment we co-render into one color image reflectivity values, attenuation coefficient values, and sound speed values. In another embodiment we co-render into one color image reflectivity values, tissue movement values, and tissue movement directions. In another embodiment we co-render into one color image reflectivity values, horizontal movement values, and vertical movement values. In another embodiment we co-render into one color image reflectivity values, Poisson's ratio values, and stiffness values. In another embodiment we co-render into one color image reflectivity values, shear wave speed values, and sound speed values. In another embodiment we co-render into one color image three properties of user choices among a list of, including but not limited to, reflectivity, attenuation coefficient, sound speed, Poisson's ratio, shear wave speed, tissue stiffness, porosity, fluid saturation, mass density, micro movement of tissue, gas bubble flow (speed and direction), and blood flow (speed and direction). We have tested our method on an in-vivo carotid ultrasound dataset. Our method is of particularly use in detailed characterization of tissues and organs, not only providing a B-mode image but also presenting two additional physical property values at the same time. This capability is not available in commercial ultrasound scanners.

The first generation of commercial ultrasound scanners in 1950s used A-mode display of ultrasound raw data. No beamforming was employed at that time. The resulting A-mode display was difficult to interpret. In 1970s the second generation of commercial ultrasound scanners used B-mode display of ultrasound images. Electronic beamforming was used, resulting in much improved ultrasound images. The B-mode display is a black-and-white display of beamformed echoes, with white colors representing strong reflectivity (impedance contrast) and black colors representing weak or no reflectivity. Color Doppler scanners came into the market in 1980s, which produced color images of blood flow on top of B-mode display. A B-mode ultrasound image is produced first. A window on the image is defined by a sonographer. Inside the window Doppler blood flow measurements are made and a color rendition of blood flow is produced and overlayed on top of the B-mode image. This is the third generation of commercial ultrasound scanners. In 1990s and early 2000s software based beamformers were developed to replace hardware-based beamforming. At the same time elastography scanners came to the market which produced color images of tissue stiffness on top of B-mode display. This is the fourth generation of commercial ultrasound scanners. The elastography display (also called E-mode) is similar to the color Doppler display, with the difference being the color display window shows tissue stiffness. Recently commercial ultrasound scanners of the fifth generation are released into the market in which data processing and beamforming are implemented on GPUs, yielding much improved ultrasound images in real time. Real time inversion of other physical properties is becoming possible.

F-Mode Ultrasound Display

We co-render into one color image of three physical properties derived from inversions of B-mode ultrasound beam data. We call the resulting display F-mode display of ultrasound images (or simply F-mode), to avoid confusion with generally accepted displays such as B-mode, C-mode, E-mode etc. In one embodiment of our method the reflectivity value (B-mode image) is mapped onto the intensity component of the YCbCr color space (Y component), the sound speed value is mapped onto a red chrome component (Cr component), and the Poisson's ratio value is mapped onto a blue chrome component (Cb component). One can change the order of the above mapping. One can also map these three properties onto the traditional RGB color space if desired. We prefer the YCbCr color space because of its superior visual effects.

Figure 1:
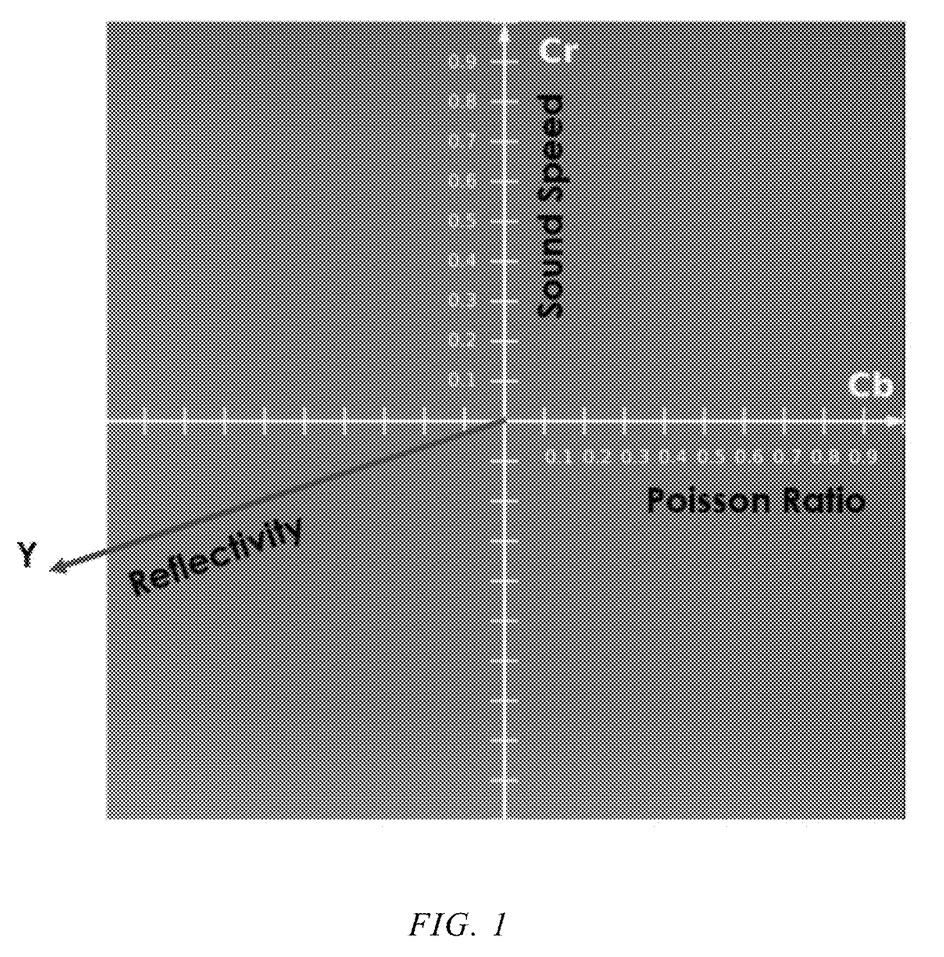
FIG. 1 shows an F-mode display of three physical attributes: reflectivity values are mapped onto the Y component of the color space; sound speed values are mapped onto the Cr component of the color space; Poisson's ratio values are mapped onto the Cb component of the color space.

The F-mode display in FIG. 1 aids in detailed analysis and characterization of tissue structures and properties, which is not possible in traditional display of ultrasound images, such as B-mode display. One can also map other properties onto the three components of YCbCr color space. The list of properties that are sensitive to ultrasound includes:

Reflectivity: acoustic impedance contrast between two tissues. A large reflectivity value is associated with strong acoustic impedance contrast (also called echoic). A small reflectivity value is associated with weak acoustic impedance contrast (also called anechoic).

Acoustic attenuation coefficient: soft tissues have exponential attenuation coefficients that are proportional to frequency. Tissue attenuation is usually expressed in the convenient units of dB/cm-MHz. The attenuation of soft tissue is generally between 0.5 to 1.0 dB/cm-MHz.

Sound speed: the speed at which a sound wave travels through tissue. The sound speed of soft tissue is generally between 1450 m/s to 1580 m/s, with an average value of 1540 m/s.

Poisson's ratio: Poisson's ratio is an important material mechanical property. The value of Poisson's ratio is 0.5 for water, or slightly less than 0.5 for soft tissues that contain a lot of water in content. Muscular tissues have Poisson's ratio in the range of 0.30~ 0.45.

Shear wave speed (and stiffness): the speed at which a shear wave travels through tissue. Stiffness is closely related to shear wave speed. Shear wave elastography is rapidly evolving US imaging technique that allows quantification of mechanical and elastic tissue properties.

Porosity and fluid saturation: bone tissues are porous media. Fluid saturation includes water saturation and oxygen saturation. Water saturation of a tissue is related to pore volume, osmotic potential, and elasticity of the tissue.

Density: mass density is measured in kg/cubic meter. The density of fat is close to 911 kg/m$^3$. Blood plasma has a density of 1020 kg/m$^3$. The density of heart muscle is close to 1081 kg/m$^3$.

Micro movement of tissues: movement of tissues between two frames, measured as displacement vectors in mm/s.

Gas bubble flow: speed and direction of contrast agents in blood vessels, measured in cm/s.

Blood flow: speed and direction of blood flows in blood vessels, measured in cm/s.

All the above properties have significant diagnostic value in ultrasound medicines [1].

In Vivo Carotid Ultrasound Data Example
PICMUS Carotid Challenge Data

PICMUS is the IEEE US 2016 Plane-wave Imaging Challenge in Medical UltraSound, an initiative of IEEE US to promote use of plane-wave ultrasound imaging modality. PICMUS carotid challenge dataset is a public domain dataset for download at Ultrasound Test Benchmark (USTB) website (www.ustb.no). The dataset contains two in vivo carotid scans, one in the cross section and another in longitudinal section, collected by a volunteer with a Verasonics Vantage 256 System and a L11 probe. The use of this dataset is subject to citation rule (www.ustb.no).

Figure 2:
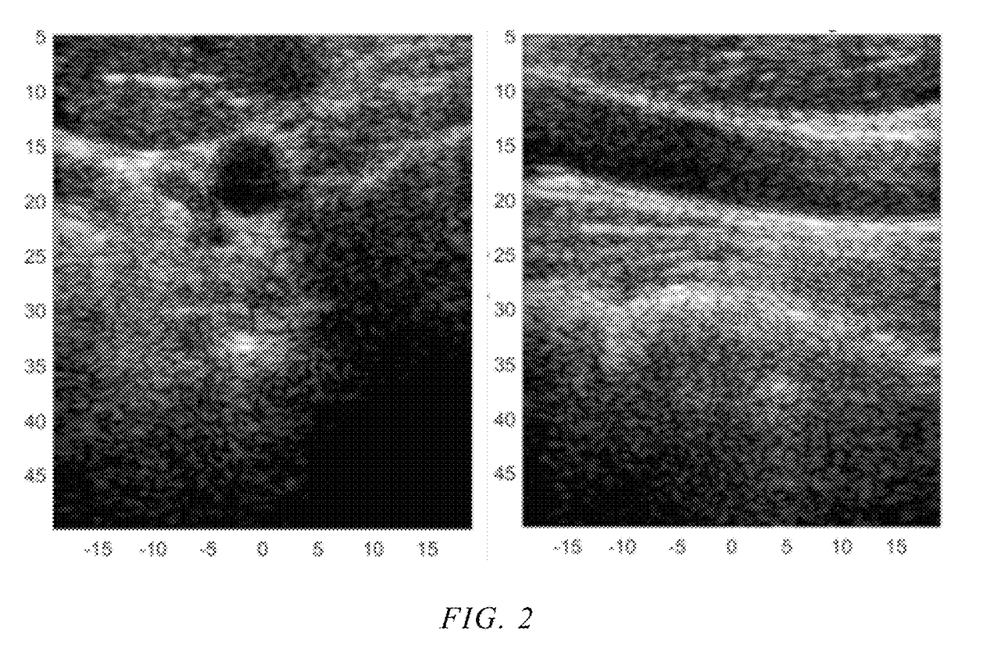
FIG. 2 shows published B-mode images on USTB website (www.ustb.no) of PICMUS carotid challenge dataset: (left) a transversal image of a neck vein, and (right) a longitudinal image of the same. All displays are in 60 dB with a log compression, with white color representing bright (large) amplitudes and black color for dim (small) amplitudes.

The images in FIG. 2 are published B-mode images on USTB website for benchmark purposes. The raw ultrasound data is collected in two directions, one measurement (left) is in a direction transversal to the neck vein in-vivo, and the other measurement (right) is in a longitudinal direction. Brighter regions represent stronger acoustic echoes. Darker regions are anechoic, with much smaller acoustic impedance contrasts. Public are invited to produce better results with improved algorithms.

Enhanced B-Mode Images

Figure 3:
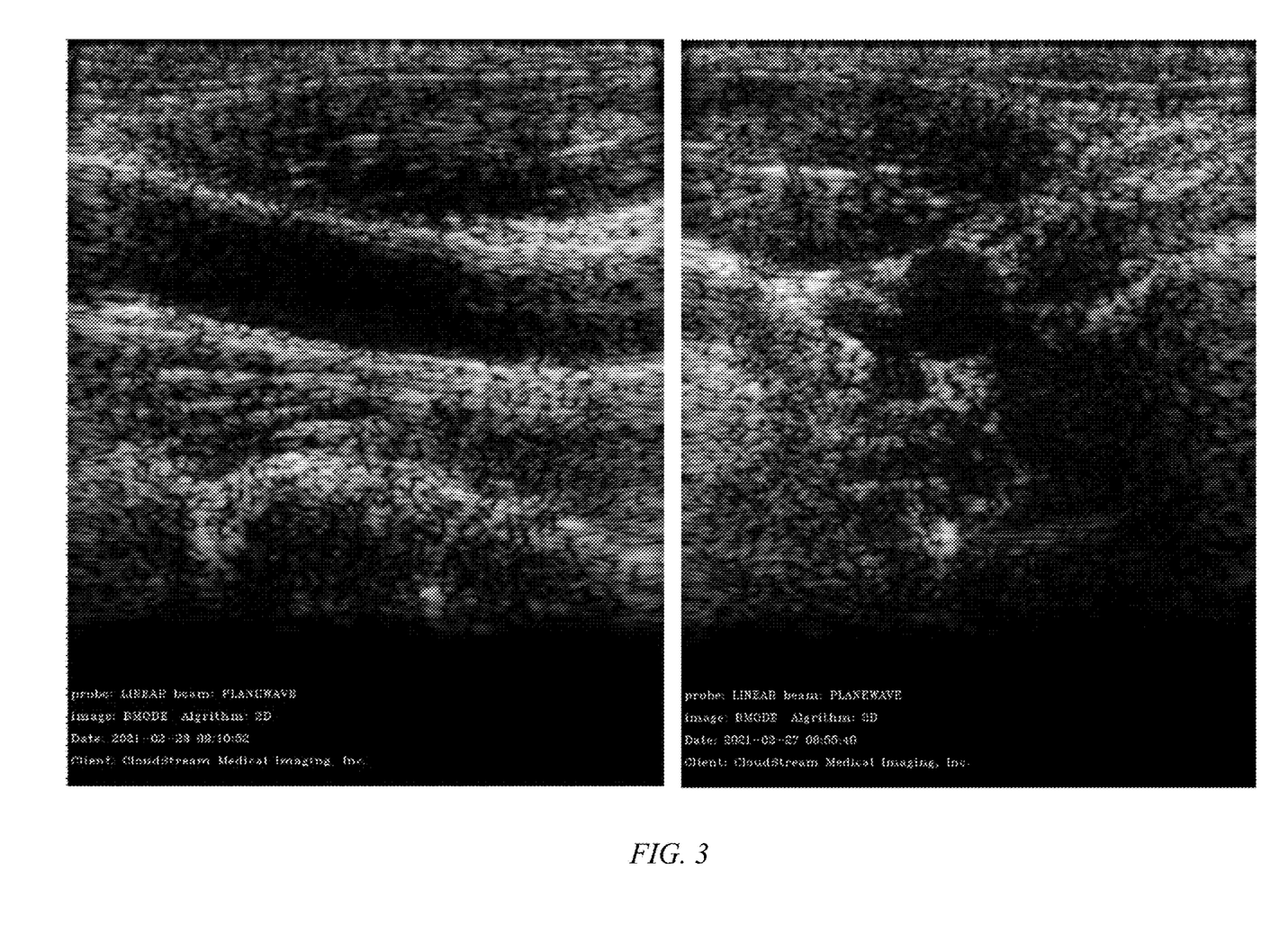
FIG. 3 shows enhanced B-mode images of the same PICMUS carotid challenge dataset obtained using the technology of the present application: (left) a transversal image of a neck vein, and (right) a longitudinal image of the same. All displays are in 60 dB with a log compression, with white color representing bright (large) amplitudes and black color for dim (small) amplitudes.

We are able to produce improved images with our technology using the same PIMCUS carotid raw ultrasound data as input [12]. FIG. 3 shows our results: improvements can be seen in both contrast resolution and spatial resolution, with clear definition of walls of carotid blood vessels (circular features on the left and elongated features on the right), showing no build-up of fatty deposits on the blood vessel walls. The dark regions are either anechoic (shallow) or acoustic waves being strongly attenuated during propagation (deep).

Sound Speed Image

Figure 4:
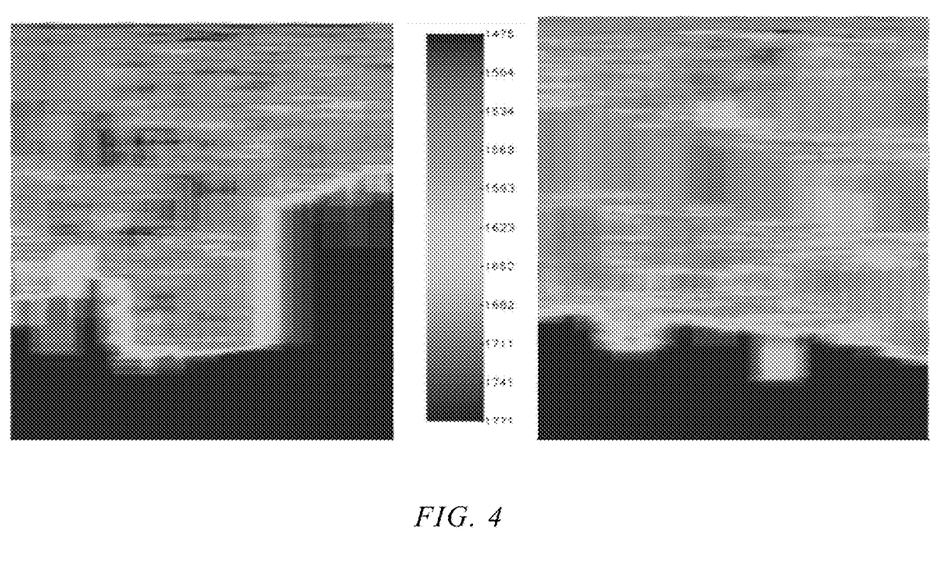
FIG. 4 shows sound speed distribution of the same PICMUS carotid challenge dataset: (left) a transversal view in sound speed of a neck vein, and (right) a longitudinal view of the same. The color bar is in m/s.

To obtain a spatially varying sound speed image we first generate a set of common image point gathers using the PICMUS carotid challenge dataset. Since sound waves in different tissues propagate with different speed values, a beamforming algorithm that utilizes a constant value for sound speed will always produce non-flat common image point gathers. The residual moveout on the common image point gathers can be accurately measured. The Dix inversion is then applied to the residual moveout measurements to obtain sound speed distribution in the image domain [12]. FIG. 4 shows the resulting sound speed images: the left one is the sound speed image in the transversal direction, and the right one is the same in the longitudinal direction. One can see lower sound speed value inside the carotid blood vessels. Soft tissues also have lower sound speed values. Muscle tissues have higher sound speed values. Since Dix inversion is one dimensional we typically see vertical stripes in the display. One can apply a spatial smoothing to remove the vertical stripes. It is worthwhile to note that the estimated values at the deep part of the images are not reliable as sound waves are strongly attenuated by tissue absorption before they can reach the transducer placed on the top surface.

Poisson's Ratio Image

Figure 5:
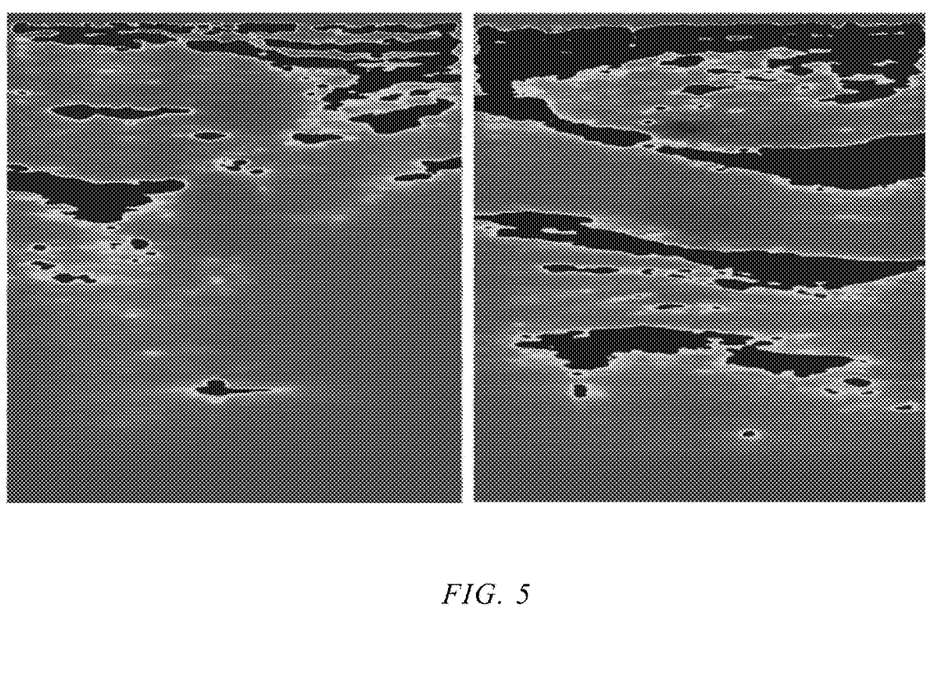
FIG. 5 shows Poisson's ratio distribution of the same PICMUS carotid challenge dataset: (left) a transversal view in Poisson's ratio (proxy) of a neck vein, and (right) a longitudinal view of the same. The color bar is in amplitude unit of the benchmark dataset.

To obtain a spatially varying Poisson's ratio image we first generate a set of common image point gathers using the PICMUS carotid challenge dataset. We then estimate B values using amplitude vs. sine squared reflection angle cross-plot [12]. The B value serves as a proxy of Poisson's ratio. Fluid and fatty tissues have larger Poisson's ratio. Muscle tissues and bones have smaller Poisson's ratio. Therefore, we can use the Poisson's ratio value to aid our characterization of physical properties of various tissues. FIG. 5 shows the resulting Poisson's ratio images (proxy): the left one is the image of Poisson's ratio in the transversal direction, and the right one is the same in the longitudinal direction. One can see higher Poisson's ratio values (bright red region) inside the blood vessels (fluid) and soft tissues. In muscular tissues the Poisson's ratio values are smaller (dark region). The Poisson's ratio image is very useful in delineating body fluids and fatty tissues.

F-Mode Display of Reflectivity, Sound Speed, and Poisson's Ratio

Figure 6:
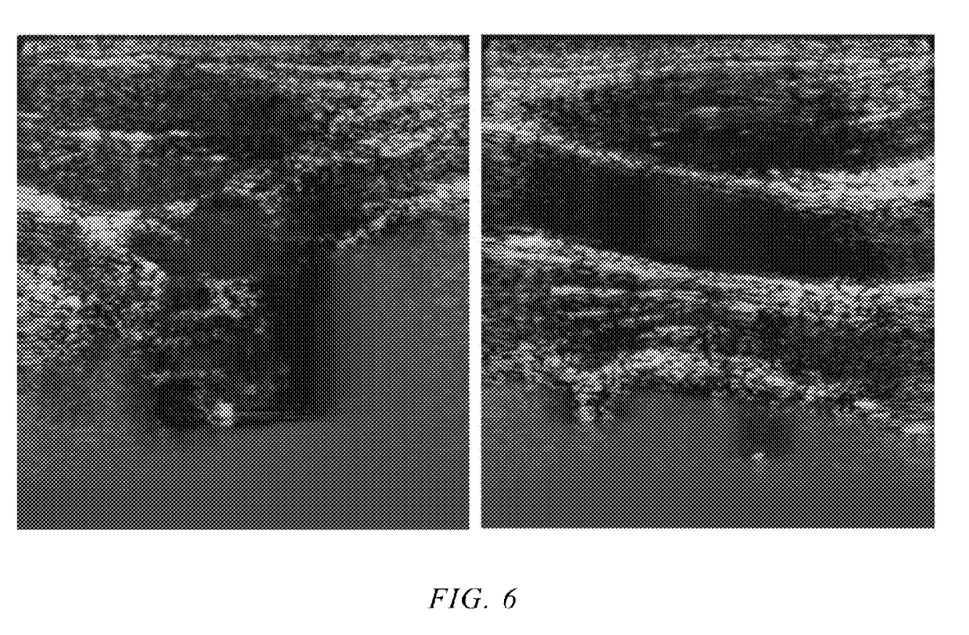
FIG. 6 shows an F-mode display of three physical attributes derived from the PICMUS carotid challenge dataset: (left) a transversal display of a neck vein, and (right) a longitudinal display of the same. The intensity component (also called Y) is proportional to reflectivity value, the blue chrome component (also called Cb) represents Poisson's ratio, and red chrome component (also called Cr) is mapped to sound speed.

We co-render into one color image of three physical properties derived from inversions of ultrasound beam data. FIG. 6 shows two F-mode images of reflectivity, sound speed, and Poisson's ratio properties obtained from inversion of the PICUS carotid challenge dataset. The left image is in the transversal direction, and the right one is in the longitudinal direction. One can clearly see internal structures and properties of tissues on F-mode displays. The carotid blood vessel is well defined in both directions, with lower sound speed values and higher Poisson's ratio values inside the blood vessel. The two walls of the blood vessel and surrounding muscular tissues show strong reflectivities, higher sound speed values, and lower Poisson's ratio values. Fatty tissues are low in reflectivity, low in sound speed value, and high in Poisson's ratio. The F-mode images aid in detailed analysis and characterization of tissue structures and properties, which is not available in traditional B-mode ultrasound scanners.

In F-mode display of three physical properties derived from ultrasound data, we map the first property (for example, reflectivity) to the Y component of a YCbCr color space, we map the second property (for example, Poisson's ratio) to the Cb component, and we map the third property (for example, sound speed) to the Cr component. The resulting display is a color image of three physical properties co-rendered together. One can clearly see reflectivity values from the Y color component (the intensity component). One can also clearly see Poisson's ratio values from the Cb color component (the blue component), with full blue color for high Poisson's ratio value and grayish color for low Poisson's ratio value. Sound speed values are visible in the Cr color component (the red component) of the display, with full red color for high sound speed value and grayish color for low sound speed value. The structural delineation of tissues is very visible on the Y component, and the property delineation of the same tissues is very visible on the Cb and Cr components. For example, in F-mode displays of ultrasound images shown in FIG. 6, a blood vessel (in deep blue color surrounded by green color) is a circular feature with higher Poisson's ratio value and lower sound speed value. If the circular feature is of higher sound speed value then it is not a blood vessel. A small cancerous feature should be of higher reflectivity value, higher sound speed value, and lower Poisson's ratio value (in bright green to yellow color). An alarm should be raised if one sees such a feature in F-mode display. On traditional B-mode display one simply could not make such a discrimination.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

REFERENCES

[1] Richard S. C. Cobbold (2007), Foundations of Biomedical Ultrasound, Oxford University Press, pages 1416-1428.
[2] F. W. Kremkau (2006), Diagnostic Ultrasound: Principles and Instruments, 7th edition, Saunders/Elsevier, St. Louis.
[3] J. S. Hwang and T. K. Song (2001), A Study of the Display Pixel-Based Focusing Method in Ultrasound Imaging, Ultrasound Imaging, Vol. 23, pages 1-18.
[4] O. M. H. Rindal (2019), Software Beamforming in Medical Ultrasound Imaging-a Blessing and a Curse, Ph.D. Thesis, University of Oslo.
[5] M. Sak, N. Duric, P. Littrup, L. Bey-Knight, H. Ali, P. Vallieres, M. E. Sherman and G. L. Gierach (2017), Using Speed of Sound Imaging to Characterize Breast Density, Ultrasound in Medicine & Biology, Vol 43, pages 91-103.
[6] C. Li, A. Stewart and N. Duric (2012), Multi-grid Tomographic Inversion for Breast Ultrasound Imaging, Proceedings of SPIE, Vol 8320, pages 1-9.
[7] J. Nebeker and T. R. Nelson (2012), Imaging of Sound Speed Using Reflection Ultrasound Tomography, Journal of Ultrasound in Medicine, Vol 31, pages 1389-1404.
[8] J. Ophir, S. K. Alam, B. S. Garra, F. Kallel, E. E. Knonfgou, T. Krousko, and C. R. B. Berritt (2002), Elastography: Imaging the Elastic Properties of Soft Tissues with Ultrasound, J. Medical Ultrasonics, Vol 29, pages 155-171.
[9] J. Bercoff, M. Tanter, T. M. Nguyen, J. M. Chassot, M. Fink, and C. Boccara (2004), Supersonic Shear Imaging: A New Technique for Soft Tissue Elasticity Mapping, IEEE Trans. On Ultrasonics, Ferroelectrics and Frequency Control, Vol 51, pages 396-409.
[10] J. Wiskin, B. Malik, D. Borup, N. Pirshafiery and J. Klock (2020), Full Wave 3D Inverse Scattering Transmission Ultrasound Tomography in the Presence of High Contrast, Nature, https://doi.org/10.1038/s41498-020-76754-3.
[11] L. Guasch, O. Calderon-Agudo, M. X. Tang, P. Nachev, and M. Warner (2020), Full-waveform Inversion Imaging of the Human Brain, Nature, https://doi.org/10.1038/s41746-020-0240-8.
[12] C. Peng (2021), Inversion of Sound Speed and Poisson's Ratio from Ultrasound Beam Data for Characterization of Tissues, U.S. Patent Appl No. 63/229,246, Filed Aug. 4, 2021.

What is claimed is:

1. A method for generating F-mode display of an ultrasound image, comprising:
    collecting ultrasound image data that include a plurality of physical properties;
    mapping the plurality of physical properties to a plurality of color components of a color space; and
    combining the color components to generate an F-mode display of the ultrasound image,
    wherein each of the plurality of physical properties corresponds to a corresponding color component, and
    wherein the plurality of physical properties are selected from the group consisting of acoustic reflectivity, acoustic attenuation coefficient, sound speed, Poisson's ratio, shear wave speed, porosity and fluid saturation, density, micro movement of tissue, gas bubble flow, and blood flow.

2. The method of claim 1, wherein an increase of a value of the corresponding color component corresponds to an increase or decrease of a value of the each of the plurality of physical properties.

3. The method of claim 1, wherein the color space is a YCbCr color space or an RGB color space.

4. The method of claim 3, wherein the plurality of physical properties are mapped to corresponding color components of the color space.

5. The method of claim 4, wherein the color space is the YCbCr color space, and the YCbCr color space includes an intensity component (Y), a red chrome component (Cr), and a blue chrome component (Cb).

6. The method of claim 5, wherein the plurality of physical properties are the reflectivity, the sound speed, and the Poisson's ratio; and the reflectivity is mapped to the intensity component, the sound speed is mapped to the red chrome component, and the Poisson's ratio is mapped to the blue chrome component.

7. The method of claim 4, wherein the color space is the RGB color space, and the RGB color space includes a red component (R), a green component (G), and a blue component (B).

8. The method of claim 7, wherein the plurality of physical properties are the reflectivity, the sound speed, and the Poisson's ratio; and the reflectivity is mapped to the red component, the sound speed is mapped to the green component, and the Poisson's ratio is mapped to the blue component.

9. An ultrasound image processing apparatus, comprising an image processor adapted to:
   collecting ultrasound image data that include a plurality of physical properties;
   mapping the plurality of physical properties to a plurality of color components of a color space; and
   combining the color components to generate an F-mode display of the ultrasound image,
   wherein each of the plurality of physical properties corresponds to a corresponding color component, and
   wherein the plurality of physical properties are selected from the group consisting of acoustic reflectivity, acoustic attenuation coefficient, sound speed, Poisson's ratio, shear wave speed, porosity and fluid saturation, density, micro movement of tissue, gas bubble flow, and blood flow.

* * * * *